United States Patent [19]

Knuebel et al.

[11] Patent Number: 5,688,976
[45] Date of Patent: Nov. 18, 1997

[54] PROCESS FOR THE PRODUCTION OF 8 α, 12-OXIDO-13,14,15,16-TETRANORLABDANE

[75] Inventors: Georg Knuebel; Andreas Bomhard, both of Duesseldorf; Ulf-Armin Schaper, Krefeld; Theo Stalberg, Monheim; Thomas Markert, Duesseldorf, all of Germany

[73] Assignee: Henkel Kommanditgesellschaft auf Aktien, Duesseldorf, Germany

[21] Appl. No.: 652,525

[22] PCT Filed: Nov. 24, 1994

[86] PCT No.: PCT/EP94/03891

§ 371 Date: Jul. 3, 1996

§ 102(e) Date: Jul. 3, 1996

[87] PCT Pub. No.: WO95/15321

PCT Pub. Date: Jun. 8, 1995

[51] Int. Cl.[6] ................................................. C07D 307/92
[52] U.S. Cl. ................................................................ 549/458
[58] Field of Search ................................................ 549/458

[56] References Cited

U.S. PATENT DOCUMENTS 3,029,255  4/1962  Stoll ........................................ 260/345.2
3,050,532  8/1962  Schumacher et al. ................. 260/343.3
5,274,134  12/1993  Bruns et al. ............................ 549/458
5,470,989  11/1995  Gerke ..................................... 549/458

FOREIGN PATENT DOCUMENTS 61-033184  2/1986  Japan .
90/12793  11/1990  WIPO .
93/02073  2/1993  WIPO .

OTHER PUBLICATIONS

Chem. Abs 105, No. 15, Oct 13, 1986, Columbus, Ohio.
Ullmanns Encyklopädie der technischen Chemie, vol. 20, p. 283, Verlag Chemie Weinheim 1981.
Helv, Chim. Acta. 1950, 33, 1310–1312.
Chem. Abstr. 57, 7316a (1962).
Chem. Abstr. 94, 15913q (1981).
Nachr. Chem. Tech. Lab 1985 (33), No. 3, p. 202.

*Primary Examiner*—Bernard Dentz
*Attorney, Agent, or Firm*—Ernest G. Szoke; Wayne C. Jaeschke; Henry E. Millson, Jr.

[57] ABSTRACT

The invention relates to a process for producing 8α,12-oxido-13,14,15,16-tetranorlabdane through the cyclizing dehydration of 8α,12-dihydroxy-13,14,15,16-tetranorlabdane in the presence of aluminophyllosilicates.

19 Claims, No Drawings

PROCESS FOR THE PRODUCTION OF 8 α, 12-OXIDO-13,14,15,16-TETRANORLABDANE

This application is a 371 of PCT/EP94/03891 filed Nov. 24, 1994.

BACKGROUND OF THE INVENTION

1. Field of the Invention

This invention relates to a process for the production of 8α,12-oxido-13,14,15,16-tetranorlabdane and to the use of special alumino layer silicates for the production of 8α,12-oxido-13,14,15,16-tetranorlabdane.

2. Statement of Related Art

8α,12-oxido-13,14,15,16-tetranorlabdane, hereinafter referred to as Ambroxan® is a valuable ambergris fragrance which is present in ambergris, a metabolic secretion of the sperm whale (Ullmanns Encyklopädie der technischen Chemie, Vol. 20, page 283, Verlag Chemie Weinheim 1981). Ambroxan® can be synthesized from sclareol by oxidative side-chain degradation and subsequent reduction of the lactone formed (sclareolide) in accordance with U.S. Pat. No. 3,050,532. The conversion of sclareolide into the odorless 8α,12-dihydroxy-13,14,15,16-tetranorlabdane, hereinafter referred to in short as diol, is carried out by methods known per se, for example by reduction with lithium aluminium hydride (Helv. Chim. Acta. 1950, 33, 1310), with sodium borohydride (Chem. Abstr. 57, 7316a) or with potassium borohydride/lithium chloride mixtures (Chem. Abstr. 94, 15913q).

The cyclizing dehydration of the diol to form Ambroxan® can be carried out with acidic catalysts, for example p-toluene sulfonic acid, p-toluene sulfonic acid chloride, catalytic quantities of sulfuric acid and acidic ion exchangers in various solvents, for example toluene, hexane, pyridine, tetrahydrofuran or methanol, preferably at boiling temperature.

U.S. Pat. No. 3,029,255 describes the use of p-naphthalene sulfonic acid or alumina as dehydration catalysts in the production of Ambroxan®. Besides resinification products and olefins, other secondary products are obtained in this that the yield of Ambroxan® is less than 77%.

JP-A-86/33184 (Takasago) describes a process for the production of Ambroxan® in which cyclization of the diol precursor is induced by special catalysts. The catalysts in question are acid-charged active bleaching earth, alumina or silica. The acids mentioned include, in particular, sulfuric acid, phosphoric acid and polyphosphoric acid. However, the Takasago process has disadvantages in regard to a) the conversion of educt, i.e. diol used, and/or
b) the formation of dehydration products (secondary products) and/or
c) the stereoselectivity of the ring closing reaction (extent of the formation of iso isomers of Ambroxan®.

The above-mentioned disadvantages of the Takasago process are obviated by the process described by applicants in earlier application WO 90/12793. However, the process according to WO 90/12793 requires relatively high reaction temperatures and relatively large quantities of catalyst. In addition, the special HCl-charged catalyst cannot readily be reused.

DESCRIPTION OF THE INVENTION

The problem addressed by the present invention was to develop a process for the production of Ambroxan® cyclizing dehydration of the diol precursor which would avoid the disadvantages of the processes known from the prior art.

It has surprisingly been found that Ambroxan® can be produced in high yields and purity if the diol precursor is subjected to cyclizing dehydration in a solvent and in the presence of alumino layer silicates which have an acid charge of 100 to 300 mval/100 g.

The expression "acid charge" in the context of the present invention applies to that part of the total acid content of the alumino layer silicates which is only loosely bound to the solid and which can be analytically determined by titration after elution with water. It is pointed out in this connection that the K catalysts have an additional acid content which is ionically bound to the skeleton of the catalyst and which does not dissociate off in aqueous dispersion.

The present invention relates to a process for the production of 8α,12-oxido-13,14,15,16-tetranorlabdane by dehydration of 8α,12-dihydroxy-13,14,15,16-tetranorlabdane (diol), in which 8α,12-dihydroxy-13,14,15,16-tetranorlabdane is subjected to cyclizing dehydration in a solvent in the presence of alumino layer silicates with an acid charge of 100 to 300 mval/100 g.

The process according to the invention has the advantage that the catalyst is only used in relatively small quantities and that most of the catalyst can be reused. In addition, only very moderate temperatures are required for carrying out the process according to the invention, so that the danger of olfactorily undesirable secondary products being formed is reduced by this particularly gentle method of production. The above-mentioned advantages of the process according to the invention are not acquired at the expense of the high stereoselectivity of the ring closing reaction known from WO 90/12793. In other words, the percentage content of the 8-epi- and 9-epi-isomers of Ambroxan® in the product is of the same order as in the process according to WO 90/12793.

Alumino layer silicates are minerals with a basic silicate structure in which silicate layers with partly incorporated aluminium$^{3+}$ ions attached to one another by dipol/dipol interactions and hydrogen bridge bonds are present, these two dimensionally infinite anionic layer silicates being electrostatically crosslinked by cations of an interlayer. The structure and composition of such layer silicates are known from the prior art and are described in the relevant literature. Examples of alumino layer silicates are talcum and clays of laminar structure, such as kaolinite, montmorillonite, bentonites and hectorites.

The quantity of dehydration catalyst, i.e. the acid-charged alumino layer silicate, is not critical per se. Normally, however, the catalyst is used in a quantity of 5 to 80% by weight, based on the diol, in the process according to the invention. In a preferred embodiment, it is used in a quantity of 15 to 35% by weight.

The ring closing reaction is carried out at temperatures in the range from 20° to 110° C., preferably at temperatures in the range from 40° to 70° C. and more preferably at temperatures in the range from 40° to 50° C.

Acid-charged alumino layer silicate is used as the dehydration catalyst in the process according to the invention. According to the invention, the acid charge is in the range from 100 to 300 mval/100 g. However, an acid charge in the range from 130 to 180 mval/100 g is particularly preferred.

Basically, there are no particular limitations to the type of acid used. However, hydrohalic acids, above all HCl, and sulfuric acid and phosphoric acid are particularly preferred.

According to the invention, acid-charged montmorillonites are particularly preferred dehydration catalysts. A particularly preferred embodiment of the present invention is characterized by the use of so-called K catalysts—which are known to the expert, for example, from Nachr. Chem. Tech. Lab. 1985 (33), No. 3, page 202—with the acid charge described above. The commercially available types KSF and KSF/0 are particularly suitable for the purposes of the invention. The K catalysts may be used individually or in combination with one another.

On the one hand, alumino layer silicates which already have the necessary critical acid charge of 100 to 300 mval/100 g from their production, as is the case for example with the K catalysts KSF and KSF/0, may be used as dehydration catalysts in accordance with the present invention. However, alumino layer silicates which initially have a relatively low acid charge from their production, but which are subsequently charged with such a quantity of acid that their acid charge is in the criticial range mentioned above, may also be used as dehydration catalysts.

The diol is typically used in water-free form. However, a diol of technical quality with a water content of up to about 2% by weight may also be used.

The present invention also relates to the use of alumino layer silicates with an acid charge of 100 to 300 mval/100 g and preferably 130 to 180 mval/100 g for the production of $8\alpha,12$-oxido-13,14,15,16-tetranorlabdane by cyclizing dehydration of $8\alpha,12$-dihydroxy-13,14,15,16-tetranorlabdane.

Suitable solvents for the cyclizing dehydration of the diol are, for example, toluene and/or xylene.

The water formed during the dehydration reaction may be removed from the reaction mixture, for example by azeotropic distillation. On completion of the dehydration reaction, the reaction mixture is worked up in known manner.

The process according to the invention may be carried out in batches or continuously. The continuous version, carried out for example in a fixed-bed reactor, affords the additional advantage that it does not require any special removal of the particulate catalyst.

The following Examples are intended to illustrate the invention without limiting it in any way.

EXAMPLES

1. General 1.1. Substances used

Diol: $8\alpha,12$-dihydroxy-13,14,15,16-tetranorlabdane

Cat-1: Active bentonite, type B (a product of Erbsloh) acid content: 80 mval $H_2SO_4$/100 g Cat-2: Silicon dioxide ("Kieselgel 60", particle size<0.063 mm; a product of Merck) charged with sulfuric acid; acid content: 200 mval $H_2SO_4$/100 g Cat-3: Neutral aluminium oxide (a product of Riedel de Haen) charged with sulfuric acid; acid content: 200 mval $H_2SO_4$/100 g Cat-4: Neutral aluminium oxide (a product of ICN) charged with hydrochloric acid; acid content: 14 mval HCl/100 g Cat-5: Catalyst KSF/0 (a product of Süd-Chemie AG); acid content: around 155 mval $H_2SO_4$/100 g 1.2 Analysis The products were quantified by gas chromatographic analysis (50 m WG11 quartz capillary; injector temperature: 220° C.; detector temperature: 250° C.; oven temperature: 80°→220° C. for a heating rate of 8° C./minute; carrier gas: nitrogen; pressure: 20 psi).

2. Description of Tests 2.1. Preparation of Ambroxan® by the process according to JP-A-86/33184 a) Comparison Example C1

51 g of n-heptanol and 2.54 g of diol were introduced into a 200 ml flask, the diol being dissolved by stirring. After the addition of 0.13 g of catalyst cat-1, the flask was evacuated to a pressure of 10 mmHg and the system was slowly heated to 40° C. under that pressure. The reaction mixture was then stirred for 3 hours at that temperature. The catalyst was filtered off, the filtrate was washed with aqueous sodium carbonate solution and the n-heptanol was subsequently distilled off in vacuo.

The Ambroxan® of 7.7%, based on diol used, was very small. The content of dehydration products was found to be 2.5%, based on Ambroxan® (cf. Table 1).

b) Comparison Example C2

In a two liter flask, a solution of 25.4 g of diol in 500 g of xylene was added to a suspension of 5 g of catalyst cat-1 in 200 ml of xylene. The flask was evacuated to a pressure of 50 mmHg and the system was slowly heated under that pressure. The reaction mixture was then refluxed for 4 hours, after which the catalyst was filtered off, the filtrate was washed with aqueous sodium carbonate solution and, finally, the xylene was distilled off.

The yield of Ambroxan® amounted to 32.2%, based on diol used. The product contained 6.0%, based on Ambroxan® of dehydration products. The content of iso isomers of Ambroxan® was 1.0%, based on diol used (cf. Table 1).

Comparison Examples C3 to C5

The operations described for Comparison Example C2 were repeated, the reaction temperature and also the type and quantity of catalyst being varied. Particulars can be found in Table 2.

The data determined in Examples C3 to C5 are set out in Table 1.

2.2. Preparation of Ambroxan® in accordance with the invention a) Example E1

600 g of technical diol (pure diol content: 90%) were dissolved in 600 ml of toluene and 120 g of the catalyst KSF/0 were added to the resulting solution which was then heated for 4 hours with stirring to 50° C. The reaction solution was then filtered off and the catalyst was extracted under reflux with 300 ml of toluene. The combined organic phases were then washed with 1% nitric acid, 1% sodium hydroxide and finally with 10% sodium sulfate solution. They were then concentrated in vacuo to dryness.

The crude product was analyzed by gas chromatography. The data determined are set out in Table 1.

The catalyst recovered was reused for the cyclization of diol. No disadvantages were observed in regard to yield or the formation of secondary products.

3. Discussion

Comparison of Example E1 according to the invention with Comparison Examples C1 to C5 shows that there are distinct differences in regard to yield and stereoselectivity. In the interests of clarity, the above-mentioned data are set out once again in Table 1. Important test parameters of Examples C1 to C5 and E1 are set out in Table 2.

TABLE 1

| Example | Ambroxan® | iso isomers of Ambroxan® | | Dehydration products[b] |
| --- | --- | --- | --- | --- |
| | | 8-epi | 9-epi | |
| C1 | 7.7% | N.d.[c] | N.d. | 2.5% |
| C2 | 32.2% | 0.9% | 0.1% | 6.0% |
| C3 | 68.1% | 3.0% | 0.1% | 17.3% |
| C4 | 66.3% | 0.8% | 0.05% | 16.1% |
| C5 | N.r.[d] | N.d. | N.d. | N.d. |
| E1 | 98.7% | <0.05% | <0.05% | 2.7% |

[a]% by weight, based on diol used
[b]% by weight, based on Ambroxan®
[c]N.d. = not determined
[d]N.r. = no reaction

TABLE 2

| Example | Temperature | Catalyst | | |
| --- | --- | --- | --- | --- |
| | | Type | Quantity[e] | Acid charge[f] |
| C1 | 40° C. | Cat-1 | 5% | 80 |
| C2 | 130° C. | Cat-1 | 20% | 80 |
| C3 | 130° C. | Cat-2 | 5% | 200 |
| C4 | 130° C. | Cat-3 | 5% | 200 |
| C5 | 50° C. | Cat-4 | 60% | 16 |
| E1 | 50° C. | Cat-5 | 20% | 155 |

[e]% by weight, based on diol used
[f]in mval/100 g catalyst

We claim:

1. In a process for the production of 8α,12-oxido-13,14,15,16-tetranorlabdane by dehydration of 8α,12-dihydroxy-13,14,15,16-tetranorlabdane (diol), the improvement wherein said diol is subjected to cyclizing dehydration in a solvent in the presence of a catalyst consisting of at least one alumino layer silicate having an acid charge of from 100 to 300 mval/100 g.

2. The process of claim 1 wherein the at least one alumino layer silicate is present in from about 5 to about 80% by weight, based on the diol.

3. The process of claim 2 wherein from about 15 to about 35% by weight of the silicate is present.

4. The process of claim 1 wherein the cyclizing dehydration is carried out at a temperature in the range of from about 40° to about 70° C.

5. The process of claim 1 wherein the at least one alumino layer silicate has an acid charge of from about 130 to about 180 mval/100 g.

6. The process of claim 1 wherein the at least one alumino layer silicate is acid charged with sulfuric acid.

7. The process of claim 1 wherein the at least one alumino layer silicate is at least one montmorillonite.

8. The process of claim 1 wherein the at least one alumino layer silicate is at least one K catalyst.

9. The process of claim 1 wherein the at least one alumino layer silicate is talcum, a kaolinite, a montmorillonite, a bentonite, and/or a hectorite.

10. The process of claim 1 wherein the cyclizing dehydration is carried out at a temperature in the range of from about 20° to about 110° C.

11. The process of claim 10 wherein said temperature is from about 40° to about 50° C.

12. The process of claim 1 wherein the at least one alumino layer silicate is acid charged with a hydrohalic acid, sulfuric acid, or phosphoric acid.

13. The process of claim 1 wherein the solvent is toluene, xylene, or a mixture thereof.

14. The process of claim 1 wherein the diol is either water-free or contains up to about 2% by weight of water.

15. The process of claim 1 wherein the at least one alumino layer silicate is reused following the cyclizing dehydration reaction.

16. The process of claim 1 wherein water formed during the cyclizing dehydration reaction is removed by azeotropic distillation.

17. In a process for the production of 8α,12-oxido-13,14,15,16-tetranorlabdane by dehydration of 8α,12-dihydroxy-13,14,15,16-tetranorlabdane (diol), the improvement wherein said diol is subjected to cyclizing dehydration at a temperature of from about 40° to about 70° C. in a solvent in the presence of from about 5 to about 80% by weight, based on the diol, of a catalyst consisting of at least one alumino layer silicate having an acid charge of from about 130 to about 180 mval/100 g.

18. The process of claim 17 wherein from about 15 to about 35% by weight of silicate is present; the diol is water-free or contains up to 2% by weight of water; and water formed during the reaction is removed by azeotropic distillation.

19. The process of claim 17 wherein the at least one alumino layer silicate is acid charged with sulfuric acid.

* * * * *